(12) United States Patent
Wright et al.

(10) Patent No.: US 7,393,541 B2
(45) Date of Patent: Jul. 1, 2008

(54) MYCOBACTERIAL VACCINE

(75) Inventors: D. Craig Wright, Pacific Grove, CA (US); Joan Brisker, Fort Lauderdale, FL (US); Mark A. Chambers, London (GB)

(73) Assignee: Novavax, Inc., Rockville, MD (US)

( * ) Notice: Subject to any disclaimer, the term of this patent is extended or adjusted under 35 U.S.C. 154(b) by 158 days.

(21) Appl. No.: 10/846,939

(22) Filed: May 13, 2004

(65) Prior Publication Data

US 2005/0118201 A1 Jun. 2, 2005

Related U.S. Application Data

(63) Continuation of application No. PCT/US02/36336, filed on Nov. 13, 2002.

(60) Provisional application No. 60/335,917, filed on Nov. 14, 2001.

(51) Int. Cl.
*A61K 39/00* (2006.01)
*A61K 39/04* (2006.01)
*A61K 39/38* (2006.01)
*A61K 45/00* (2006.01)
*A01N 65/00* (2006.01)
*A01N 63/00* (2006.01)
*A01N 1/00* (2006.01)

(52) U.S. Cl. .................... 424/248.1; 424/420; 424/450; 424/184.1; 424/234.1; 424/278.1; 424/280.1; 424/93.1; 424/93.4; 435/243; 435/253.1

(58) Field of Classification Search ............. 424/184.1, 424/278.1, 280.1, 200.1, 93.1, 248.1, 93.4, 424/450, 420, 234.1; 435/243, 253.1, 863–865
See application file for complete search history.

(56) References Cited

U.S. PATENT DOCUMENTS

| | | | | |
|---|---|---|---|---|
| 5,474,848 A | * | 12/1995 | Wallach | 428/402.2 |
| 6,290,987 B1 | | 9/2001 | Modi | |
| 6,387,373 B1 | * | 5/2002 | Wright et al. | 424/192.1 |
| 6,649,172 B2 | * | 11/2003 | Johnson | 424/278.1 |
| 6,936,260 B1 | * | 8/2005 | Schroder et al. | 424/248.1 |
| 2004/0133160 A1 | * | 7/2004 | Dalton | 604/117 |
| 2005/0118201 A1 | * | 6/2005 | Wright et al. | 424/248.1 |
| 2005/0175630 A1 | * | 8/2005 | Raz et al. | 424/203.1 |

FOREIGN PATENT DOCUMENTS

WO WO 00/47225 8/2000
WO WO 03/051288 A2 * 6/2003

OTHER PUBLICATIONS

World Health Organization. Global Tuberculosis Control. WHO Reprot 2001. Geneva, Switzerland, WHO/CDS/TB/2001:287, pp. 1-34.*
Orme, Microbes and Infection, 2005, 7:905-910.*
Griffin et al, Trends in Microbiology, Nov. 1995, 3/11:418-424.*
Andersen, Trends in Immunology, Mar. 2001, 22/3:160-168.*
McMurray, International J. Parasitology, 2003, 33:547-554.*
Smith et al, Clinical Infectious Diseases, 2000, 31(Suppl. 3):S68-S70.*
Girard et al, Vaccine, 2005, Article in Press, 7 pp.*
Orme, Vaccine, 2005, Article in Press, 18 pp.*
Reed et al, Microbes and Infection, 2005, 7:922-931.*
Orme, Vaccine, 2005, 23:2105-2108.*
Lima et al, Vaccine, 2004, 22:2374-2379.*
O'Hagan et al, Biomolecular Engineering, 2001, 18:69-85.*
Chambers et al, Vaccine, 2004, 22:1063-1071.*
Buddle, Tuberculosis, 2001, 81/1-2:125-132.*
Guleria et al, Nature Medicine, 1996, 2/3:334-337.*
Robertson et al, Vaccine, 2002, 20:31-41.*
Andersen, Scand. J. Immunol., 1997, 45:115-131.*
Bachmann et al, DDT, Jun. 2001, 6/11:566-568.*
Wiegeshaus et al, Reviews Infectious Diseases, 1989, 11/Suppl. 2:S484-S490.*
Vogel, Clinical Infectious Diseases, 2000, 30/Suppl. 3:S266-S270.*
Vogel et al In: Vaccine Design: The Subunits and Adjuvant Approach, editors Powell et al, 1995, pp. 141, 186-187.*
PCT International Preliminary Examination Report PCT/US02/36336, filed Nov. 13, 2002.
Griffin, J.F.T., et al., Animal models of protective immuni in tuberculosis to evaluate candidate vaccines. Trends in Microbiology, Nov. 1995, vol. 3, No. 11, pp. 418-424.
Smith, D., et al., Animal Models for Experimental Tuberculosis. Clinical Infectious Diseases. 2000, vol. 31, supplement 3, pp. S68-S70.
Wiegeshaus, E.H., et al., Evaluation of the Protective Potency of New Tuberculosis Vaccines. Reviews of Infectious Diseases. Mar. 1989, vol. 11, Supplement 2, pp. S484-S490.
International Search Report for International Application No. PCT/US02/36336.

* cited by examiner

*Primary Examiner*—Nita Minnifield
(74) *Attorney, Agent, or Firm*—Ralph A. Loren; Edwards Angell Palmer & Dodge, LLP

(57) ABSTRACT

Compositions and methods for enhancing the immunity of a subject or vaccinating a subject against mycobacterial infections are disclosed. The invention provides compositions comprising formalin inactivated cultures of a mycobacterium, such as *M. bovis*, and a Novasome® adjuvant, as well as methods for using such compositions.

11 Claims, No Drawings

MYCOBACTERIAL VACCINE

This Application is a Continuation of application PCT/US02/36336 filed on Nov. 13, 2002. PCT/US02/36336 is a Non-Prov of Prov (35 USC 119(e)) application 60/335917 filed on Nov. 14, 2001.

BACKGROUND OF THE INVENTION

The genus mycobacterium is responsible for more suffering worldwide than all other bacterial genera combined. Mycobacteria are classified into two broad categories. The first category, the *M. tuberculosis* complex, includes *M. tuberculosis, M. bovis, M. microtti*, and *M. africanus*. The second category includes all other species and is referred to as nontuberculosis mycobacteria (NTM) or mycobacteria other than tubercule bacilli (MOTT) which includes, among others, *M. kansasii, M. marinum, M. similae, M. scrofulaceum, M. szulgai, M. gordonae, M. avium, M. intracellulare, M. ulcerans, M. fortuitum, M. chelonae, M. xenopi*, and *M. malmoense*. Currently, over 60 species of mycobacteria have been defined. Of all the culturable mycobacteria, only *M. tuberculosis* is an obligate pathogen.

Tuberculosis (TB) which is caused by infection with *M. tuberculosis* or *M. bovis* remains one of the most significant diseases of man and animals (1-3) and continues to inflict a huge cost on society with regard to human and animal health and financial resources (4-7). The only vaccine currently available for the prevention of TB is a live attenuated vaccine, Bacille Calmette-Guerin (BCG), derived from *Mycobacterium bovis*. BCG possesses many of the qualities of an ideal vaccine: it is cheap to produce and administer, it is safe and has been shown to be efficacious in many circumstances, especially against severe and fatal tuberculosis in children (8). However, BCG has been found to give variable efficacy in a number of clinical trials. In the Medical Research Council trial in the United Kingdom, BCG imparted 77% protection (9) while, at the other end of the spectrum, in the largest clinical trial in India it exhibited zero protective efficacy (10). Although BCG generally gives poor protection against pulmonary tuberculosis in adults, it remains the "gold-standard" against which candidate TB vaccines of improved efficacy are measured. With the advent of the HIV/AIDS pandemic, concern has been raised over the safety of BCG. Since BCG can be pathogenic in situations of compromised or deficient immunity (11), vaccination with BCG can be contraindicated for those very individuals most at risk of contracting tuberculosis.

Problems surrounding the lack of universal efficacy and safety of BCG have resulted in increased efforts to develop a new generation of tuberculosis vaccines. One approach being pursued is the generation of subunit vaccines requiring inoculation of mycobacterial nucleic acid, protein(s) or peptides in adjuvant. While individual proteins generally have only marginal efficacy, protein mixes work much better (12), suggesting immunity to numerous antigens is required for full protection. This is supported by the observation that DNA vaccination with multiple antigens has an additive effect on protective efficacy (13). Another approach has used molecular genetic tools to generate mutant members of the TB complex that are attenuated and avirulent to an immunocompromised host (14). For example, deletion of genes involved in amino acid and purine biosynthesis resulted in auxotrophic mutants of BCG that were unable to persist in both immunocompetent (15, 16) and severely immunocompromised mice (17). However, the mutants were able to persist long enough to express metabolic antigens and engender a degree of protective immunity. It has been suggested that such mutants could be used to vaccinate individuals at risk of developing compromised or deficient immunity (17), although concerns remain regarding the use of genetically modified live vaccines in either humans or livestock (14, 18).

Vaccines based on killed whole cell preparations of mycobacteria have classically conferred little to no specific protection to subsequent challenge with virulent mycobacteria (19-22), presumably because the important protective antigens are only expressed when the bacteria are metabolically active (21, 23, 24). There are exceptions to this (25, 26) and it has been proposed that in terms of generating protective immunity, the particular antigens that are presented may be less important than the way in which they are presented (27, 28). The majority of vaccination studies with killed preparations of mycobacteria have used heat as the method of killing. However, this treatment may significantly denature important antigens and could account for the disappointing results generally seen with such vaccines (29). An alternative to heat inactivation is treatment with formalin. Formalin inactivation was first used in the 1920's to detoxify the diphtheria toxin isolated from cultures of *Corynebacterium diphtheriae* (30, 31); the approach still used for the production of the vaccine (32). Formalin treatment of whole mycobacteria has the advantage of killing the organism while retaining the antigenic integrity of many of the proteins present (33).

SUMMARY OF THE INVENTION

The present invention provides compositions and methods for enhancing the immunity of a subject or vaccinating a subject against infection by mycobacteria. In particular, as part of the present invention, it was discovered that formalin inactivated preparations of mycobacteria, e.g., *M. bovis*, mixed with a variety of non-phospholipid liposome adjuvants (Novasomes®) conferred protection from lethal aerogenic challenge with *M. bovis* when administered to guinea pigs by subcutaneous inoculation. Accordingly, the compositions and methods of the present invention include formalin inactivated cultures of mycobacteria, e.g., mycobacteria from the *M. tuberculosis* complex or mycobacteria from the NTM complex, and a Novasome® adjuvant. Novasome® adjuvants, as defined herein, are paucilamellar liposomes containing non-phospholipids, sterols, oils and buffer and are described in U.S. Pat. No. 5,474,848, incorporated herein in its entirety by reference. In a preferred embodiment, the Novasome® adjuvant is NAX M687.

As demonstrated in the studies described herein, the compositions of the present invention can be used to protect against infections caused by mycobacteria, such as tuberculosis. Thus, in one embodiment, the invention provides a compositions comprising formalin inactivated cultures of a mycobacterium and a Novasome® adjuvant.

In another embodiment, the invention provides a method of enhancing the immunity of a subject against mycobacteria or vaccinating a subject against mycobacteria, such as *M. bovis*, by administering to the subject a composition comprising formalin inactivated cultures of mycobacteria and a Novasome® adjuvant.

Compositions of the present invention can be administered to a subject using any suitable route of administration. Typically the compositions are administered by injection, in an appropriate amount and dosage regimen, to achieve a therapeutic effect.

Other features and advantages of the instant invention be apparent from the following detailed description and claims.

DETAILED DESCRIPTION OF THE INVENTION

The present invention provides compositions and methods for enhancing the immunity of a subject or vaccinating a subject against infection by mycobacteria, such as tuberculosis. The compositions of the invention include a formalin inactivated culture of mycobacteria and a Novasome® adjuvant. Formalin inactivated mycobacteria encompassed by the present invention include both mycobacteria of the *M. tuberculosis* complex and mycobacteria of the nontuberculosis mycobacteria complex (NTM). Examples of mycobacteria from the *M. tuberculosis* complex include *M. tuberculosis, M. bovis, M. microtti, M. africanus*, and Bacille Calmette-Guerin (BCG). Examples of mycobacteria from the NTM complex include, among others, *M. kansasii, M. marinum, M. similae, M. scrofulaceum, M. szulgai, M. gordonae, M. avium, M. intracellulare, M. ulcerans, M. fortuitum, M. chelonae, M. xenopi*, and *M. malmoense*.

As demonstrated in the studies described herein, the formalin inactivated cultures were found to be completely nonviable as determined by culture on growth medium and inoculation into severe combined immunodeficient (SCID) mice. The formalin-inactivated preparations were mixed with a range of Novasome® adjuvants (paucilamellar liposomes composed of non-phospholipids, sterols, oils and buffer) and were administered to guinea pigs. The preparations produced no adverse reaction in the animals. In fact, a number of the treated guinea pigs were protected from challenge with a low dose aerosol of viable *M. bovis*. In some cases, the levels of protection were equivalent to that achieved with the gold-standard vaccine, live BCG Pasteur.

Vaccines based on killed whole mycobacteria cell preparations have advantages in respect of their safety and the fact that they represent a complex mix of protein and non-protein antigens. Also, the immune response to killed mycobacterial vaccines is less restricted by the genetics of the host than with live BCG (26). However, such vaccines are not widely used due to the numerous studies reporting their inability to confer protective immunity (19-22). In studies where such vaccines were found to be efficacious, an oil adjuvant had to be used or the vaccine administered in multiple doses via inappropriate routes (e.g., intraperitoneal) to achieve protection (27, 38-40). When given intracutaneously, such a vaccine failed to protect (41).

The present invention uses mild formalin fixation to retain the antigenicity of the preparations coupled with the use of new generation non-phospholipid liposome adjuvants (Novasomes®), previously demonstrated to induce a Th1 response (42, 43). As demonstrated in the studies described below, these formulations provide protection against mycobacteria aerogenic challenge in guinea pigs equivalent to that achieved with live BCG. Such protection can be achieved with a single dose of vaccine administered, for example, subcutaneously. As reported for *M. tuberculosis* (21), killed BCG vaccines without adjuvant conferred no protection against challenge with *M. bovis*. However, formalin-inactivated *M. bovis* in the absence of adjuvant did confer protection to the lung, which shows that BCG lacks the full repertoire of cell-associated protective antigens potentially expressed by *M. bovis*.

In a particular embodiment, the Novasome® liposomes were designed to have a net negative charge. Negatively charged liposomes are removed more rapidly from the circulation, localised more rapidly in the liver, spleen and bone marrow, and are more effectively trapped in the lungs than neutral or positively charged liposomes (44).

The least effective adjuvant was NAX 57, the only Novasome® adjuvant not to include MPL (monophosphoryl lipid A). MPL has already been shown to have adjuvant properties in a variety of mycobacterial vaccine/challenge models (45-47) and lipid A in the context of liposomes activates macrophages for antigen presentation (48, 49). The best vaccine/adjuvant combination was formalin-inactivated *M. bovis* plus NAX M687. This conferred protection against death and growth of *M. bovis* in the lungs and spleen statistically equivalent to either live BCG Pasteur or BCG Tokyo. NAX M687 contains both MPL and batyl alcohol, the latter also having macrophage activating properties (50). The adjuvanticity of Novasomes®, NAX M687 in particular, is due in part to their propensity to target lymphoid tissue and the lung, as well as to activate macrophages. All Novasomes® are biodegradable by the oxidative metabolic processes resident in macrophages (51), although the fusogenicity of liposomes influences where their cargo is delivered at the subcellular level. Fusogenic liposomes are deliver their cargo directly to the cytosol, making antigens available for presentation by MHC class I molecules to CD8$^+$ T-cells (52, 53). In contrast, non-fusogenic liposomes will enter the endosomal pathway where their antigenic cargo will be degraded for presentation by MHC class II molecules to CD4$^+$ T-cells (52, 53). NAX M687 is the only non-fusogenic Novasome® described herein.

Consistent with the reported ability of live BCG to protect against disseminated tuberculosis (54, 55), some of the formalin-inactivated BCG vaccines gave significant protection to the spleen, although all failed to protect the lung. Formalin-inactivated *M. bovis* plus NAX M687 was the only killed vaccine that protected both the lung and spleen from bacterial replication. This is due, in part, to the fact that different cell wall-associated antigens are responsible for tissue-specific growth and dissemination of TB complex mycobacteria: the lipid phthiocerol dimycocerosate (PDIM) is required for growth in the lungs but not the spleen or liver (56); and heparin-binding haemagglutinin adhesin (HBHA) is required for extrapulmonary dissemination (57). Since PDIM and HBHA are associated with the mycobacterial cell wall, an immune response directed to these molecules (or others like them) determines whether protection is expressed in the lungs or spleen or both. In fact, coating BCG with anti-HBHA antibodies impaired dissemination of the bacteria after intranasal infection (57).

Whether live or formalin-inactivated, no difference was found in the efficacy of the two BCG strains against *M. bovis* challenge. This is in contrast to previous studies performed in mice and humans, in which BCG Pasteur conferred a superior level of protection over BCG Tokyo against *M. tuberculosis* (58, 59). BCG Pasteur and BCG Tokyo express different amounts of the cell wall-associated antigen, MPB83 (60). Although this antigen is immunodominant in natural *M. bovis* infection (61, 62) and is a protective antigen in mice (63), the results described herein show that it is not the dominant protective antigen of the BCG vaccines.

The vaccine formulations of the present invention are cheap and safe to produce (at least compared to the BCG formulations) and had no reactogenicity in the naive guinea pig.

The present invention is further illustrated by the following examples which should not be construed as further limiting. The contents of all figures and all references, patents and published patent applications cited throughout this application are expressly incorporated herein by reference. Those skilled in the art will recognize, or be able to ascertain using no more than routine experimentation, many equivalents to the specific embodiments of the invention described herein. Such equivalents are intended to be encompassed by the following Examples and claims.

EXAMPLES

Materials and Methods

Bacterial strains and treatment with formalin: BCG Pasteur and Tokyo strains were obtained from the Statens Serum Institut, Copenhagen, Denmark. The strain of *M. bovis* used in this study (2122/97) was isolated from a tuberculin test reactor cow in 1997 and propagated at VLA Weybridge. Four week old cultures of all strains, grown in M-ADC-TW broth (34) supplemented with 0.2% (v/v) glycerol (BCG) or 4.16 mg/ml sodium pyruvate (*M bovis*), were harvested by centrifugation. The bacterial cells were resuspended in 1.5% (v/v) formalin in PBS to a concentration of 0.25 g wet weight of bacterial cells per ml. The cultures were stirred at 4° C. for 96 hours and then harvested by centrifugation at 4° C. The formalin-treated cells were washed once with PBS and stored at 4° C. until needed.

Validation of formalin-inactivation: An aliquot of each preparation of formalin-treated cells, representing approximately $2.5 \times 10^7$ CFU, were plated on Middlebrook 7H10 agar plus 10% (v/v) Middlebrook OADC enrichment and incubated for six weeks. A further aliquot of identical size was injected into three groups of five SCID beige mice (maintained at CAMR) subcutaneously in the nape. The mice were monitored for clinical signs of disease for 12 weeks at which point they were killed and examined for the presence of tubercles lesions in the internal organs.

Formulation with adjuvants: Each preparation of formalin-treated cells was mixed with the following negatively-charged Novasome® (non-phospholipid liposome) adjuvants: NAX 57 (fusogenic; made with polyoxyethylene-2-cetyl ether, e.g., Brij 56); NAX M57 (fusogenic; made with polyoxyethylene-2-cetyl ether plus monophosphoryl lipid A (MPL)); NAX M77 (fusogenic; made with polyoxyethylene-2-stearyl ether, i.e., Brij 71, plus MPL); NAX M687 (non-fusogenic; made with glycerol monostearate and batyl alcohol plus MPL). The cells were resuspended in the adjuvant using a tuberculin syringe fitted with an 18 gauge needle and then fully homogenised by passing the suspension back and forth between two tuberculin syringes forty times. A control preparation of each mycobacterium was generated in the same way but using sterile water in place of the adjuvant.

Vaccination and challenge of guinea pigs: Female Dunkin-Hartley guinea pigs weighing between 350-450 g and free of intercurrent infection were obtained from Charles River UK Ltd., Margate, UK. Groups of six guinea pigs were immunised with 100 µl of each formalin-treated vaccine/adjuvant formulation subcutaneously in the nape and another six, with a live suspension of $5 \times 10^4$ CFU BCG Tokyo. Two further control groups of 18 guinea pigs were vaccinated with $5 \times 10^4$ CFU live BCG Pasteur or PBS alone. Five weeks after vaccination all guinea pigs were challenged aerogenically with a live suspension of *M. bovis* 2122/97 to achieve an inhaled retained dose in the lungs of approximately 10 organisms (35). Two additional guinea pigs were vaccinated with the formalin-treated/water preparation but were left unchallenged in order to confirm the sterility of the vaccine.

Post mortem examination of guinea pigs: Animals were killed by peritoneal overdose of sodium pentobarbitone ten weeks after challenge or when an individual had lost 20% of its maximal body weight (the humane endpoint), whichever was the sooner. Examination was carried out immediately after death. External assessment of body condition was followed by gross internal examination of the neck region, and thoracic and abdominal cavities. The lungs were cut along the medial line; the left lung placed into 5 ml sterile water for bacteriology and the right lung placed in 10% formal buffered saline for later gross examination. The whole spleen was removed aseptically and placed into 5 ml sterile distilled water for bacteriology.

Bacterial enumeration: Lungs and spleens were homogenized in 5 ml sterile distilled water using a rotating blade macerator system. Viable counts were performed on serial dilutions of the macerate and examined after 4 weeks incubation at 37° C. for growth of mycobacteria.

Statistical analyses: Appropriate statistical tests were chosen and all data analysed using the InStat software package (version 3.00, GraphPad, San Diego, Calif.). The survival data was analysed using Fisher's Exact Test. The Unpaired t test was applied to the bacteriology data since each data set under analysis was tested and found to come from a population that followed Gaussian distribution.

Example 1

Formalin Treatment Renders Cultures Non-viable

A 100 µl aliquot, representing approximately $2.5 \times 10^7$ CFU of formalin-treated BCG Pasteur, BCG Tokyo and *M. bovis* 2122/97 was plated onto solid medium and injected into SCID beige mice in order to test whether formalin treatment had killed the mycobacteria. No bacteria were cultured and all challenged mice survived 12 weeks with no clinical signs of disease. On post mortem examination, no lesions were observed in the internal organs of any mouse.

Two mice were vaccinated with formalin-treated *M. bovis* in water but left unchallenged. Fifteen weeks later the mice were killed and examined for signs of tuberculosis. No lesions were observed in the internal organs of either animals and no bacteria were cultured from the spleens and lungs.

Example 2

Formalin-inactivated Novasome® Adjuvanted Vaccines Protect Guinea Pigs from Challenge with *M. bovis*

Having established that the formalin-inactivated vaccines were non-viable, their protective efficacy was tested using the guinea pig low-dose *M. bovis* aerosol challenge model previously described (35). No adverse reactions were observed at the vaccination site of any animal throughout the experiment. Following challenge with *M. bovis*, varying numbers of guinea pigs in each group had to be killed before the end of the experiment because they had reached the humane endpoint. Table 1 shows the number of animals in each treatment group that survived to the end of the experiment. At least one adjuvant formulation for each strain of vaccine conferred significant survival on the group compared with the PBS control. Vaccination with live preparations of BCG Pasteur and BCG Tokyo also conferred significant survival.

TABLE 1

Ability of vaccines to protect guinea pigs against lethal aerogenic infection with *M. bovis*

| Vaccine/ adjuvant combination | Number surviving to end of experiment: No adjuvant | NAX 57 | NAX M57 | NAX M77 | NAX M687 |
|---|---|---|---|---|---|
| PBS | 3 (18) | ND | ND | ND | ND |
| Live BCG | 15 (18)*** | ND | ND | ND | ND |

TABLE 1-continued Ability of vaccines to protect guinea pigs against lethal aerogenic infection with *M. bovis*

| Vaccine/adjuvant combination | Number surviving to end of experiment | | | | |
|---|---|---|---|---|---|
| | No adjuvant | NAX 57 | NAX M57 | NAX M77 | NAX M687 |
| Pasteur Live BCG Tokyo | 5 (6)** | ND | ND | ND | ND |
| Formalin-inactivated *M. bovis* | 1 (6) | 1 (6) | 1 (6) | 1 (6) | 4 (6)* |
| Formalin-inactivated BCG Pasteur | 2 (6) | 2 (6) | 3 (6) | 3 (6) | 5 (6)** |
| Formalin-inactivated BCG Tokyo | 1 (6) | 5 (6)** | 4 (6)* | 0 (6) | 1 (6) |

Number of animals per group is shown in parenthesis.
*P < 0.05, P < 0.01, *P < 0.001 (compared with PBS group, using Fisher's Exact test).
ND, not done.

Homogenates of lung and spleen from each guinea pig at the time of death were plated for the enumeration of *M. bovis*. Table 2 and Table 3 show the yield of *M. bovis* from the lungs and the spleen, respectively, of vaccinated guinea pigs ten weeks after aerogenic infection with *M. bovis*. Only formalin-inactivated formulations based on *M. bovis* conferred significant protection against bacterial replication in the lung (Table 2). One of these formulations (*M. bovis*—NAX M687) also conferred significant protection on the spleen (Table 3). In contrast, four of the formalin-inactivated BCG vaccines conferred significant protection to the spleen, although not to the lung. Vaccination with live preparations of BCG Pasteur and BCG Tokyo significantly reduced the bacterial load in both the lung and spleen. No formalin-inactivated vaccine in the absence of adjuvant had any significant protective effect, with the exception that formalin-inactivated *M. bovis* in water gave a small (0.58 $\log_{10}$) but significant (p<0.05, t-test) reduction in the number of bacteria cultured from the lung.

TABLE 2

Yield of *M. bovis* from the lungs of vaccinated guinea pigs ten weeks after aerogenic infection with *M. bovis*

| Vaccine/adjuvant combination | $\log_{10}$ CFU ± SE | | | | |
|---|---|---|---|---|---|
| | No adjuvant | NAX 57 | NAX M57 | NAX M77 | NAX M687 |
| PBS | 6.34 ± 0.17 | ND | ND | ND | ND |
| Live BCG Pasteur | 4.99 ± 0.24 (1.34)*** | ND | ND | ND | ND |
| Live BCG Tokyo | 4.92 ± 0.25 (1.42)*** | ND | ND | ND | ND |
| Formalin-inactivated *M. bovis* | 5.76 ± 0.08 (0.58)* | 5.70 ± 0.02 (0.64) | 5.51 ± 0.24 (0.83)* | 5.52 ± 0.05 (0.82)* | 4.97 ± 0.25 (1.37)** |
| Formalin-inactivated BCG Pasteur | 6.50 ± 0.19 (−0.16) | 6.07 ± 0.31 (0.27) | 6.05 ± 0.10 (0.29) | 5.73 ± 0.14 (0.60) | 5.68 ± 0.32 (0.66) |
| Formalin-inactivated BCG Tokyo | 5.61 ± 0.32 (0.73) | 5.90 ± 0.18 (0.43) | 5.58 ± 0.30 (0.76) | 6.32 ± 0.10 (0.02) | 6.33 ± 0.16 (0.01) |

$\log_{10}$ protection compared with PBS group is shown in parenthesis.
*P < 0.05, P < 0.01, *P < 0.001 (compared with PBS group, using t-test).
ND, not done.

TABLE 3

Yield of *M. bovis* from the spleens of vaccinated guinea pigs ten weeks after aerogenic infection with *M. bovis*

| Vaccine/adjuvant Combination | $\log_{10}$ CFU ± SE | | | | |
|---|---|---|---|---|---|
| | No adjuvant | NAX 57 | NAX M57 | NAX M77 | NAX M687 |
| PBS | 5.32 ± 0.20 | ND | ND | ND | ND |
| Live BCG Pasteur | 3.38 ± 0.24 (1.94)**** | ND | ND | ND | ND |
| Live BCG Tokyo | 3.87 ± 0.38 (1.45)** | ND | ND | ND | ND |
| Formalin-inactivated *M. bovis* | 4.67 ± 0.12 (0.65) | 5.19 ± 0.17 (0.13) | 5.29 ± 0.18 (0.04) | 5.04 ± 0.25 (0.28) | 4.27 ± 0.38 (1.05)* |
| Formalin-inactivated | 4.73 ± 0.26 (0.59) | 5.63 ± 0.21 (−0.31) | 4.74 ± 0.05 (0.58) | 3.85 ± 0.17 (1.47)*** | 4.20 ± 0.32 (1.12)* |

TABLE 3-continued

Yield of *M. bovis* from the spleens of vaccinated guinea pigs ten weeks after aerogenic infection with *M. bovis*

| Vaccine/adjuvant Combination | Log$_{10}$ CFU ± SE | | | | |
|---|---|---|---|---|---|
| | No adjuvant | NAX 57 | NAX M57 | NAX M77 | NAX M687 |
| BCG Pasteur Formalin-inactivated BCG Tokyo | 4.51 ± 0.33 (0.81) | 4.65 ± 0.19 (0.67) | 3.81 ± 0.41 (1.51)** | 4.95 ± 0.15 (0.37) | 3.97 ± 0.45 (1.35)* |

Log$_{10}$ protection compared with PBS group is shown in parenthesis.
*$P < 0.05$, $P < 0.01$, *$P < 0.001$, ****$P < 0.0001$ (compared with PBS group, using t-test).
ND, not done.

The extent of gross pulmonary tuberculosis in the right lung of each animal was assessed by weight (pre-fixation), by counting the number of lesions visible on the surface of the lung and assigning a score based on lesion size and severity (post-fixation) (36). By these criteria, no vaccine influenced gross pulmonary tuberculosis, including the two live BCG vaccines (data not shown).

Accordingly, at least one formalin-inactivated formulation based on *M. bovis* conferred significant protection against bacterial replication in both the lungs and the spleen.

REFERENCES

1. Grange, J. M. & Collins, C. H. (1987) *Epidemiol Infect* 99, 221-34.
2. Salo, W. L., Aufderheide, A. C., Buikstra, J. & Holcomb, T. A. (1994) *Proc Natl Acad Sci USA* 91, 2091-4.
3. Crubezy, E., Ludes, B., Poveda, J. D., Clayton, J., Crouau-Roy, B. & Montagnon, D. (1998) *C R Acad Sci III* 321, 941-51.
4. Dankner, W. M., Waecker, N. J., Essey, M. A., Moser, K., Thompson, M. & Davis, C. E. (1993) *Medicine (Baltimore)* 72, 11-37.
5. O'Reilly, L. M. & Daborn, C. J. (1995) *Tuber Lung Dis* 76 Suppl 1, 1-46.
6. Steele, J. H. (1995) in *Mycobacterium bovis Infection in Animals and Humans*, eds. Thoen, C. O. & Steele, J. H. (Iowa State University Press, Ames), pp. 47-61.
7. Krebs, J. R. (1997) (Ministry of Agriculture, Fisheries and Food Publications, London, UK, London).
8. Bloom, B. R. & Fine, P. E. M. (1994) in *Tuberculosis: Pathogenicity, Protection, and Control*, ed. Bloom, B. R. (American Society for Microbiology, Washington), pp. 531-57.
9. Hart, P. D. & Sutherland, I. (1977) *Br Med J* 2, 293-5.
10. Tuberculosis (1980) *Indian J. Med. Res.* 72(suppl.), 1-74.
11. Williams, D. E. (1995) in *Mycobacterium bovis Infection in Animals and Humans*, eds. Thoen, C. O. & Steele, J. H. (Iowa State University Press, Ames), pp. 47-61.
12. Orme, I. M., McMurray, D. N. & Belisle, J. T. (2001) *Trends Microbiol* 9, 115-118.
13. Morris, S., Kelley, C., Howard, A., Li, Z. & Collins, F. (2000) *Vaccine* 18, 2155-63.
14. Collins, D. M. (2000) *Immunol Cell Biol* 78, 342-8.
15. McAdam, R. A., Weisbrod, T. R., Martin, J., Scuderi, J. D., Brown, A. M., Cirillo, J. D.,.Bloom, B. R. & Jacobs, W. R., Jr. (1995) *Infect Immun* 63, 1004-12.
16. Jackson, M., Phalen, S. W., Lagranderie, M., Ensergueix, D., Chavarot, P., Marchal, G., McMurray, D. N., Gicquel, B. & Guilhot, C. (1999) *Infect Immun* 67, 2867-73.
17. Guleria, I., Teitelbaum, R., McAdam, R. A., Kalpana, G., Jacobs, W. R., Jr. & Bloom, B. R. (1996) *Nat Med* 2, 334-7.
18. Hewinson, R. G. (2001) *Tuberculosis*.
19. Bloch, H. & Segal, W. (1955) *Am Rev Tuberc Pulm Dis* 71.
20. Youmans, G. P. (1979) in *Tuberculosis*, ed. Youmans, G. P. (W. B. Saunders, pp. 225-35.
21. Orme, I. M. (1988) *Infect Immun* 56, 3310-2.
22. Abou-Zeid, C., Gares, M. P., Inwald, J., Janssen, R., Zhang, Y., Young, D. B., Hetzel, C., Lamb, J. R., Baldwin, S. L., Orme, I. M., Yeremeev, V., Nikonenko, B. V. & Apt, A. S. (1997) *Infect Immun* 65, 1856-62.
23. Andersen, P., Askgaard, D., Ljungqvist, L., Bentzon, M. W. & Heron, I. (1991) *Infect Immun* 59, 1558-63.
24. Wiker, H. G. & Harboe, M. (1992) *Microbiol Rev* 56, 648-61.
25. Paterson, J. C., Crombie, D. W. & Coles, J. C. (1949) *Can J Res* 27, 37-42.
26. Singh, I. G., Mukherjee, R. & Talwar, G. P. (1991) *Vaccine* 9, 10-4.
27. Anacker, R. L., Barclay, W. R., Brehmer, W., Goode, G., List, R. H., Ribi, E. & Tarmina, D. F. (1969) *Am Rev Respir Dis* 99, 242-8.
28. Lowrie, D. B., Tascon, R. E. & Silva, C. L. (1995) *Int Arch Allergy Immunol* 108, 309-12.
29. Dubos, R. J., Schaefer, W. B. & Pierce, C. H. (1953) *J Exper Med* 97, 221-33.
30. Glenny & Hopkins (1923) *Br J Exp Pathol* 4, 283-288.
31. Ramon (1924) *Ann I Inst Pasteur* 38, 1-10.
32. European (1995) in *European Pharmacopoeia*, pp. 756.
33. Carabias, E., Palenque, E., Serrano, R., Aguado, J. M. & Ballestin, C. (1998) *Apmis* 106, 385-8.
34. Jacobs, W. R., Jr., Kalpana, G. V., Cirillo, J. D., Pascopella, L., Snapper, S. B., Udani, R. A., Jones, W., Barletta, R. G. & Bloom, B. R. (1991) *Methods Enzymol* 204, 537-55.
35. Chambers, M. A., Williams, A., Gavier-Widen, D., Whelan, A., Hughes, C., Hall, G., Lever, M. S., Marsh, P. D. & Hewinson, R. G. (2001) *Vet Microbiol* 80, 213-226.
36. Chambers, M. A., Williams, A., Gavier-Widen, D., Whelan, A., Hall, G., Marsh, P. D., Bloom, B. R., Jacobs, W. R. & Hewinson, R. G. (2000) *Infect Immun* 68, 7094-7099.
37. Andersen, P. (1994) *Infect Immun* 62, 2536-2544.
38. Olson, B. J., Habel, K. & Piggott, W. R. (1947) *Pub Health Rep* 62, 293-296.
39. Sarber, R. W., Nungester, W. J. & Stimpert, F. D. (1950) *Am Rev Tuberc* 62, 418-427.
40. Milzer, A., Levinson, S. O. & Lewis, M. B. (1950) *Proc Soc Exper Biol Med* 75, 733-6.

41. Seagle, J. B., Karlson, A. G. & Feldman, W. H. (1952) *Am Rev Tuberc* 67, 341-353.
42. Gupta, R. K., Varanelli, C. L., Griffin, P., Wallach, D. F. H. & Siber, G. R. (1996) *Vaccine* 14, 219-225.
43. Zimmerman, D. H., Ulrich, J. T., Wright, C., Lloyd, J. P., Winship, M. D. & Sarin, P. S. (1998) *AIDS Res Hum Retrovir* 14, 741-749.
44. Fidler, I. J. & Schroit, A. J. (1986) *Symp Fundam Cancer Res* 38, 183-207.
45. Baldwin, S. L., D'Souza, C., Roberts, A. D., Kelly, B. P., Frank, A. A., Lui, M. A., Ulmer, J. B., Huygen, K., McMurray, D. M. & Orme, I. M. (1998) *Infect Immun* 66, 2951-9.
46. Brandt, L., Elhay, M., Rosenkrands, I., Lindblad, E. B. & Andersen, P. (2000) *Infect Immun* 68, 791-795.
47. Wedlock, D. N., Vesosky, B., Skinner, M. A., De Lisle, G. W., Orme, I. M. & Buddle, B. M. (2000) *Infect Immun* 68, 5809-5815.
48. Richards, R. L., Hayre, M. D., Hockmeyer, W. T. & Alving, C. R. (1988) *Infect Immun* 56, 682-686.
49. Alving, C. R., Verma, J. N., Rao, M., Krzych, U., Amselem, S., Green, S. M. & Wassef, N. M. (1992) *Res Immunol* 143, 197-198.
50. Yamamoto, N., St Claire, D. A. J., Homma, S. & Ngwenya, B. Z. (1988) *Cancer Res* 48, 6044-6049.
51. Wallach, D. F. H. & Philippot, J. R. (1993) in *Liposome Technology: Liposome preparation and related techniques* (CRC Press, Boca Raton, Fla.), pp. 141-156.
52. Gregoriadis, G. (1995) *Trends Biotech* 13, 527-537.
53. Janeway, C. A., Travers, P., Walport, M. & Shlomchik, M. (2001) in *Immunobiology: the immune system in health and disease*, ed. Gibbs, S. (Garland Publishing, New York), pp. 155-184.
54. Fok, J. S., Ho, R. S., Arora, P. K., Harding, G. E. & Smith, D. W. (1976) *J Infect Dis* 133, 137-44.
55. Rodrigues, L. C., Diwan, V. K. & Wheeler, J. G. (1993) *Int J Epidemiol* 22, 1154-8.
56. Cox, J. S., Chen, B., McNeil, M. & Jacobs, W. R. (1999) *Nature* 402, 79-83.
57. Pethe, K., Alonso, S., Biet, F., Delogu, G., Brennan, M. J., Locht, C. & Menozzi, F. D. (2001) *Nature* 412, 190-194.
58. Gheorghiu, M. & Lagrange, P. H. (1983) *Ann Immunol (Paris)* 134C, 125-147.
59. ten Dam, H. G. (1993) in *Tuberculosis*, eds. Reichman, L. B. & Hershfield, E. S. (Marcel Dekker, New York), pp. 251-269.
60. Wiker, H. G., Nagai, S., Hewinson, R. G., Russell, W. P. & Harboe, M. (1996) *Scand J Immunol* 43, 374-380.
61. Fifis, T., Corner, L. A., Rothel, J. S. & Wood, P. R. (1994) *Scand J. Immunol.* 39, 267-74.
62. O'Loan, C., Pollock, J., Hanna, J. & Neill, S. (1994) *Clin Diagn Lab Immunol* 1, 608-11.
63. Chambers, M. A., Vordermeier, H., Whelan, A., Commander, N., Tascon, R., Lowrie, D. & Hewinson, R. G. (2000) *Clin Infect Dis* 30 Suppl 3, S283-7.
64. Freudenstein, H., Weinmann, E. & Hill, I. (1988) *Vaccine* 6, 315-27.
65. Rook, G. A. W. & Bloom, B. R. (1994) in *Tuberculosis: Pathogenesis, protection, and control*, ed. Bloom, B. R. (American Society for Microbiology, Washington, D.C.), pp. 485-501.
66. Wayne, L. G. & Sramek, H. A. (1979) *Infect Immun* 24, 363-370.
67. Andersen, P., Askgaard, D., Ljungqvist, L., Bennedsen, J. & Heron, I. (1991) *Infect Immun* 59, 1905 -1910.

Incorporation by Reference

All patents, pending patent applications and other publications cited herein are hereby incorporated by reference in their entirety.

Equivalents

Those skilled in the art will recognize, or be able to ascertain using no more than routine experimentation, many equivalents to the specific embodiments of the invention described herein. Such equivalents are intended to be encompassed by the following claims.

What is claimed as new and desired to be protected by letters Patent of the United States is:

1. An adjuvanted vaccine for producing an in vivo T cell-mediated immune response to a mycobacterium in a mammalian subject, said vaccine comprising an effective amount of a formalin-inactivated *Mycobacterium bovis* and an adjuvant, said adjuvant comprising oil-containing nonphospholipid paucilamellar lipid vesicles comprising monophosphoryl lipid (MPL) and batyl alcohol.

2. The vaccine of claim 1 wherein the mycobacterium is selected from the group consisting of *M. bovis* strains Bacille Calmette-Guerin (BCG) Pasteur and BCG Tokyo.

3. The vaccine of claim 1, wherein the lipid vesicles are negatively charged.

4. The vaccine of claim 1, wherein the lipid vesicles are non-fusogenic.

5. The vaccine of claim 1, wherein the vaccine targets the lymphoid tissue or the lungs of the subject.

6. The vaccine of claim 1, wherein the vaccine activates macrophages in the subject.

7. The vaccine of claim 1, wherein the vaccine initiates a Th1 immune response in the subject.

8. A method for vaccinating a mammalian subject against tuberculosis, comprising administering the vaccine of claim 1.

9. The method of claim 8, wherein the subject is challenged with a viable mycobacterium in aerosol form.

10. The method of claim 9, wherein the mycobacterium is *M. bovis*-strain Bacille Calmette-Guerin (BCG).

11. The method of claim 8, wherein the step of administering protects the lung and the spleen from tuberculosis replication.

* * * * *